United States Patent [19]

Praderio

[11] Patent Number: 4,494,653
[45] Date of Patent: Jan. 22, 1985

[54] CONTAINER FOR SURGICAL PATTIES

[75] Inventor: Joseph J. Praderio, Quincy, Mass.

[73] Assignee: Codman & Shurtleff, Randolph, Mass.

[21] Appl. No.: 601,455

[22] Filed: Apr. 18, 1984

[51] Int. Cl.³ .................. A61F 13/00; B65D 1/36; B65D 81/36; B65D 85/62

[52] U.S. Cl. .................. 206/370; 206/205; 206/210; 206/388; 206/490; 206/362; 206/459; 206/438

[58] Field of Search ............ 206/370, 362, 388, 205, 206/210, 490, 459, 438

[56] References Cited

U.S. PATENT DOCUMENTS

| 822,060 | 5/1906 | Lawler | 206/388 |
|---|---|---|---|
| 1,762,558 | 6/1930 | Mitchell | 206/490 |
| 3,481,462 | 12/1969 | Chapel | 206/438 |
| 3,630,202 | 12/1971 | Small | 206/370 |
| 3,759,375 | 9/1973 | Nappi | 206/362 |
| 3,819,039 | 6/1974 | Erickson | 206/388 |
| 3,948,390 | 4/1976 | Ferreri | 206/370 |

*Primary Examiner*—William T. Dixson, Jr.
*Attorney, Agent, or Firm*—Donal B. Tobin

[57] ABSTRACT

A container for a plurality of surgical patties having a recess for receiving a number of surgical patties and a plurality of count slots for receiving locating strings attached to the patties so that each pattie may be readily counted by surgical personnel. Additional slots are provided so that the locating strings can be wound back across the pattie recess to hold the patties in the recess during shipping. Wetting fluid may be introduced into the recesses to wet the patties before they are used in the body. If a plurality of pattie recesses are used, channel recesses are provided to provide fluid communication between the pattie recesses to that wetting fluid may be distributed among the multiple recesses.

11 Claims, 2 Drawing Figures

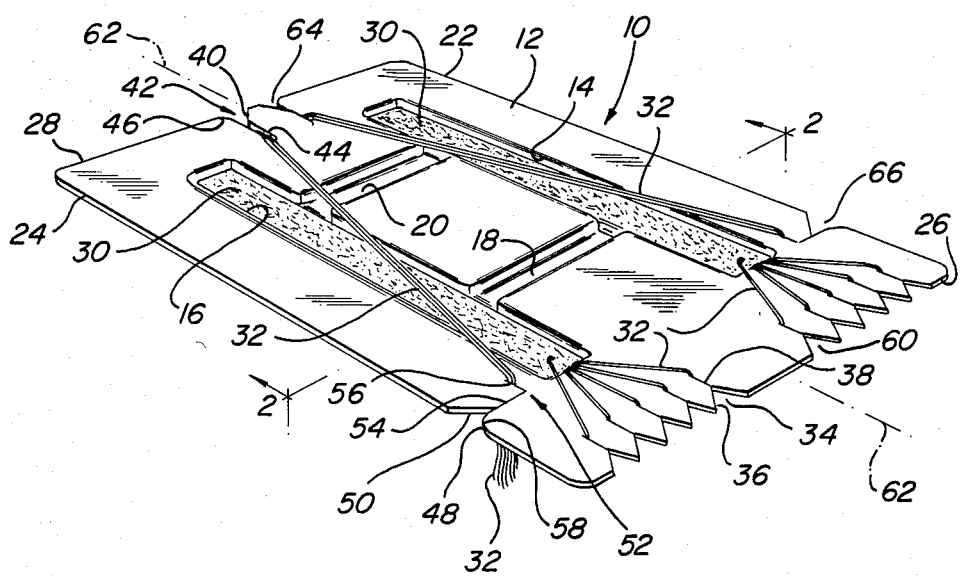
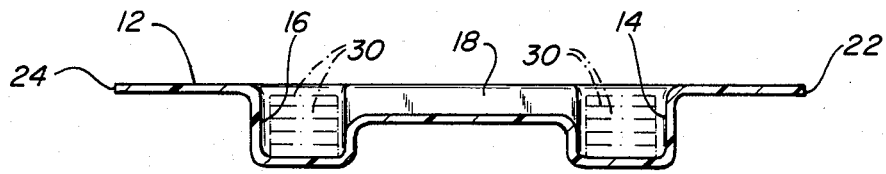

CONTAINER FOR SURGICAL PATTIES

FIELD OF THE INVENTION

The present invention relates to a container used in packaging surgical patties and particularly a container which can also serve as a tray for soaking the patties in a wetting solution.

BACKGROUND OF THE INVENTION

Surgical patties are thin absorbent strips of material which are used to absorb body fluids during surgical procedures and/or to protect delicate tissue from damage during surgery. Surgical patties come in a variety of sizes and shapes. A locating string is usually attached to these patties to serve as a means for locating the pattie in the surgical site. The locating string is usually several inches long and can be traced back to the pattie so that a pattie will not be inadvertently left within the surgical site after the operation has been completed.

As pointed out in a variety of patents, for example U.S. Pat. No. 3,481,462 entitled Disposable Surgical Holder and Counter, it is necessary that all surgical patties used in the operating room be counted before they are used and after they are retrieved from the surgical site. A variety of packages have been provided to facilitate this counting procedure so that surgical patties are not left in the surgical site.

It is sometimes necessary to soak these surgical patties in sterile water or in saline solution or some other liquid. This soaking procedure requires the patties to be removed from their counter package and saturated in fluid just before they are inserted within the surgical site. It would be desirable to have a container for surgical patties which would provide a ready accounting for the patties both before they were introduced to and after they were removed from the surgical site. It would also be desirable to have a container which could also function as a tray in which patties could be soaked prior to insertion in the surgical site.

SUMMARY OF THE INVENTION

The present invention provides a container for a number of surgical patties which can be used as an accounting card for patties both before they are placed into and after they are collected from the surgical site. The container also can be used as a tray for soaking the patties before they are introduced into the surgical site. The container also has a variety of slots which permit locating strings attached to the patties to be wound in such a way as to hold the patties in the container during shipment so that the patties do not move around during shipment and so that the locating strings do not become tangled during shipment.

The container of the present invention includes a base of plastic material in which one or more recesses are formed to hold a plurality of surgical patties. An array of count slots are provided on the edge of the base into which the locating strings which are attached to each end individual pattie may be placed. The edge of the base also includes a collection slot in which the several locating strings may all be collected and a tie-down slot located on the edge of the base in a position transverse to the pattie recess from the collection slot so that the locating strings may be stretched across the patties to hold them in the recess.

Two or more pattie recesses may be used, and they may be connected by one or more channel recesses. The channel recesses are recessed into the base a distance less than the pattie recesses. This permits a minimum amount of wetting fluid to be maintained in each pattie recess and to inhibit the wetting fluid from all flowing into one pattie recess.

The count slots, collection slot and tie down slot all have V-shaped entry notches to facilitate the entry of the strings into the respective slots.

In the preferred embodiment the base is generally rectangular and includes two pattie recesses connected by two channel recesses. The count slots, collection slots and tie-down slots are respectively disposed symmetrically on the edge of the base.

The container is designed to be inserted within a sterile package after the surgical patties have been placed in the container.

These and other features and advantages of the present invention will become apparant from the following detailed description of the preferred embodiment taken in conjunction with the following drawings.

BRIEF DESCRIPTION OF THE DRAWINGS

FIG. 1 shows a perspective view of the container of the present invention; and

FIG. 2 shows a sectional view of the invention shown in FIG. 1.

DETAILED DESCRIPTION OF THE PREFERRED EMBODIMENT

Referring now to FIG. 1 there is shown a perspective view of the container 10 of the present invention which is made of a thin sheet 12 of generally rectangular plastic into which first and second pattie recesses 14 and 16 are formed by a well known thermoforming process. Channel recesses 18 and 20 are also formed in sheet 12 and connect pattie recesses 14 and 16. It can be seen, particularly in FIG. 2, that a channel recesses 18 and 20 are recessed a depth less than the depth of pattie recesses 14 and 16. This permits a quantity of wetting fluid to be maintained in both pattie recesses 14 and 16 even though container 10 may be slightly tipped in one direction or another. This inhibits the flow of all of the wetting fluid into one or the other of pattie recesses 14 or 16.

It can be seen that pattie recesses 14 and 16 and channel recesses 18 and 20 are symmetrically placed on generally rectangular sheet 12. Rectangular sheet 12 has a first and second side 22 and 24, respectively, and a first and second end 26 and 28, respectively.

In this prefered embodiment each of pattie recesses 14 and 16 holds a number, preferably five of patties 30 each of which has attached to it a locating string 32.

The first end 26 of sheet 12 includes an array of count slots 34. Each count slot 34 is provided to hold one of the locating strings of the patties which are placed in the adjoining pattie recess 14 or 16. Each count slot 34 has a generally V-shaped entry guide 36 and a slit 38 extending into surface 12 from the base of V-shaped guide 36. Each of slits 38 is designed to hold one locating string 32.

The other end 28 of sheet 12 includes a collecting slot 40 into which each of the locating strings 32 from the patties 30 in pattie recess 16 are placed. Collection slot 40 includes a V-shaped entry guide 42 and a slit 44. One side 46 of guide 42 is formed on a convex radius.

A tie-down slot 48 is placed on one side 24 of sheet 12 on the oposite side of recess 16 from collection slot 40 so that the collected locating strings 32 may be stretched across pattie recess 16 to hold patties 30 in place during shipment. This prevents patties 30 from falling out of recess 16 during shipment and prevents locating strings 32 from becoming tangled. It is not necessary that all locating strings 32 for the patties in recess 16 be stretched across recess 16. One locating string would be sufficient to hold patties 30 in recess 16. However, for convenience, it is believed desirable to stretch all of the location strings 32 for the patties in recess 16 across recess 16. Tie-down slot 48 has a V-shaped entry guide 50 and an L-shaped slit 52. One leg 54 of slit 52 extends generally perpendicular to side 24. The other leg 56 of slit 52 extends in the direction toward collection slot 40. Like collection slot 40, one side 58 of the guide 50 forms a convex curve.

Sheet 12 also includes a second array of count slots 60 for the patties placed in recess 14. Count slots 60 are the same as count slots 34 and may be symmetrically arranged along end 26 about the longitudinal center line 62 of sheet 12. A separate collection slot 64 and a second tie-down slot 66 are provided for the surgical patties placed in recess 14. Each of these slots 64, 66 and 60 are designed like the corresponding slots for the surgical patties placed in pattie recess 16 on sheet 12.

The container of the preferred embodiment shown in FIG. 1 is used by stacking five surgical patties 30 in recess 16 so that there is sufficient clearance around the edges of patties 30 to permit them to be easily inserted and removed from recess 16 and to permit a quantity of wetting liquid to be added to recess 16 to soak the patties. A locating string 32 from each separate pattie 30 is placed in each one of the five count slots 34. Locating strings 32 are then stretched across the bottom of sheet 12 and into collection slot 40. Strings 32 are then stretched across pattie recess 16 together into tie down slot 48. Strings 32 are moved transversely along leg 54 of tie down slot 48 and then longitudinally into longitudinal leg 56 so that the strings 32 may be pulled tightly across the surface of patties 30 held in recess 16. A like number of patties is similarly placed in recess 14. The entire container is then placed in a sterile package for shipment.

When the sterile package is opened and container 10 is removed from the package, a quantity of sterile wetting fluid, either sterile water or saline solution or some other suitable fluid, may be placed in recesses 14 and 16 to wet patties 30 before they are placed into the surgical site. One need not be careful in applying this liquid, because a quantity of liquid introduced into either pattie recess 14 or 16 will be transferred to the other pattie recess by means of transverse channel recesses 18 or 20. It will be noted, particularly in FIG. 2, that the depth of channel recesses 18 and 20 is less than the depth of pattie recesses 14 and 16, so that a quantity of wetting fluid will remain in each of pattie recesses 14 and 16 and will not all flow into one channel if container 10 becomes slightly tilted.

It will also be appreciated that when the operating room personnel are using the patties and the container, the container 10 provides a good accounting method so that the user will know how many patties were present at the beginning of the operation merely be counting the strings placed in count slots 34 and 60, respectively. After a surgical pattie is used, it is removed from the surgical site, and its locating string 32 is placed in the proper count slot 34 or 60 from which it was taken. When an operation starts, the surgical personnel know that 10 surgical patties are present. When the operation is over, there should be 10 surgical patties present, whether they are used or not.

The present invention has been described in conjunction with the preferred embodiment. Those skilled in the art will appreciate that many modifications and changes may be made in the present embodiment without departing from the scope of the present invention. It is, therefore, not intended to limit the present invention except as set forth in the appended claims.

I claim:

1. A container for a plurality of surgical patties comprising:
   a base and a peripheral edge;
   a recess formed in said base, said recess adapted to receive a plurality of patties each having a locating string attached thereto;
   a portion of said edge adjacent one end of said recess having a corresponding plurality of count slots therein, each slot adapted to receive the locating string of one of said plurality of patties;
   another portion of said edge disposed adjacent the other end of said recess including a collection slot for receiving all of said strings;
   a tie-down slot disposed on a third portion of said edge spaced transversely of said recess from said collection slot and positioned such that a locating string extending from said collection slot to said tie down slot extends across said recess so as to permit said locating strings to act as a means for holding said plurality of patties within said recess;
   said recess adapted for receiving a wetting solution for said patties.

2. The container of claim 1 further including a second recess in said base for containing a plurality of surgical patties, said edge further including an array of count slots and a tie down slot associated with said second recess;
   at least one channel recess in said base providing fluid communication between said first and second recesses.

3. The container of claim 2 further including an additional collection slot associated with said second recess.

4. The container of claim 2 wherein said channel recess is recessed a distance less than said pattie recesses so that a minimum amount of wetting fluid will be retained in each of said pattie recesses.

5. The container of claim 1 where each of said count slots includes a generally V-shaped entry guide portion adapted for guiding location strings into said count slots.

6. The container of claim 1 wherein said collection slot includes a generally V-shaped entry guide portion and said collection slot extends in a direction generally opposed to said count slots.

7. The container of claim 1 wherein said tie-down slot includes a generally L-shaped configuration with one leg of said "L" extending generally transversed to the direction of said collection slot and the other leg of said "L" extending in a direction toward said collection slot; said tie-down slot further including a V-shaped entry guide portion.

8. The container of claim 2 wherein said base includes a generally rectangular peripheral edge having first and second opposed ends and first and second opposed sides.

said pattie recesses extending generally parallel to each other and parallel to said opposed first and second sides;

at least two channel recesses extending between said pattie recesses and providing fluid communication there between;

said count slots for each of said pattie recess disposed symmetrically on said first of said opposite ends;

said tie-down slot for one pattie recess disposed on one opposed side and said tie down slot for the other pattie recess disposed on the other of said opposite sides.

9. The container of claim 7 wherein said pattie recesses and said channel recesses are symmetrically disposed on said base; and, said count slots and said tie-down slots also symmetrically arranged on said base.

10. The container of claim 2 wherein said base includes a generally rectangular peripheral edge having a first and second opposed sides and first and second opposed ends; and, wherein said count slots for one of said pattie recesses are arranged on said first end of said base end; and, said count slots for the other pattie recess are arranged on said second opposed end of said base.

11. The container of claim 6 wherein one leg of said generally V-shaped entry guide includes a curved portion providing a convex radius for said one leg.

* * * * *